(12) United States Patent
Grandolfo

(10) Patent No.: US 8,870,825 B2
(45) Date of Patent: Oct. 28, 2014

(54) EXTERNAL END DEVICE FOR PERMANENT CATHETERS

(76) Inventor: Nicola Grandolfo, Triggiano (IT)

( * ) Notice: Subject to any disclaimer, the term of this patent is extended or adjusted under 35 U.S.C. 154(b) by 381 days.

(21) Appl. No.: 13/378,543

(22) PCT Filed: Jun. 15, 2010

(86) PCT No.: PCT/IT2010/000269
§ 371 (c)(1),
(2), (4) Date: Dec. 15, 2011

(87) PCT Pub. No.: WO2010/146614
PCT Pub. Date: Dec. 23, 2010

(65) Prior Publication Data
US 2012/0089096 A1    Apr. 12, 2012

(30) Foreign Application Priority Data
Jun. 16, 2009   (IT) .............................. BA2009A0026

(51) Int. Cl.
| | | |
|---|---|---|
| *A61M 5/32* | (2006.01) | |
| *A61M 1/36* | (2006.01) | |
| *A61M 39/16* | (2006.01) | |
| *A61M 39/22* | (2006.01) | |
| *A61M 39/00* | (2006.01) | |
| *A61M 39/10* | (2006.01) | |
| *A61M 39/02* | (2006.01) | |

(52) U.S. Cl.
CPC ........... *A61M 39/165* (2013.01); *A61M 1/3661* (2014.02); *A61M 1/3653* (2013.01); *A61M 2039/0009* (2013.01); *A61M 2039/1077* (2013.01); *A61M 39/0247* (2013.01); *A61M 39/22* (2013.01); *A61M 2039/229* (2013.01)
USPC ........................................................ 604/175

(58) Field of Classification Search
USPC ................... 604/48, 93.01, 174, 175
See application file for complete search history.

(56) References Cited

U.S. PATENT DOCUMENTS

| | | | | | |
|---|---|---|---|---|---|
| 4,242,310 | A | * | 12/1980 | Greff et al. ..................... | 422/300 |
| 5,167,638 | A | * | 12/1992 | Felix et al. ..................... | 604/175 |
| 5,324,274 | A | * | 6/1994 | Martin .......................... | 604/248 |
| 6,156,016 | A | * | 12/2000 | Maginot ....................... | 604/264 |
| 7,347,853 | B2 | * | 3/2008 | DiFiore et al. ................ | 604/537 |
| 2004/0097903 | A1 | * | 5/2004 | Raulerson ..................... | 604/523 |
| 2007/0083156 | A1 | * | 4/2007 | Muto et al. ................ | 604/93.01 |

FOREIGN PATENT DOCUMENTS

| | | |
|---|---|---|
| EP | 0 070 087 | 1/1983 |
| EP | 0 227 219 | 7/1987 |

OTHER PUBLICATIONS

International Search Report dated Dec. 23, 2010, corresponding to PCT/IT2010/000269.

* cited by examiner

*Primary Examiner* — Nicholas Lucchesi
*Assistant Examiner* — Diva K Chander
(74) *Attorney, Agent, or Firm* — Young & Thompson

(57) ABSTRACT

An external end device for permanent catheters includes a container that houses two taps being provided with knobs and having, at one hand, a first connector for the connection to the catheters and, at the other hand, second connectors projecting from the container for the connection to an external equipment. The first connector is connected to the catheter by a coupling exiting the container and externally holding a subcutaneous cuff designed to be positioned in the subcutaneous tissue of the patient's body. The second connectors are provided with caps surrounded by the disposable absorbent material being received in the closure lid and having spaces for housing the caps for protecting them externally from a bacterial attack by the antiseptic substance by which it is impregnated. Further an implantation method of the device in a patient is disclosed.

10 Claims, 6 Drawing Sheets

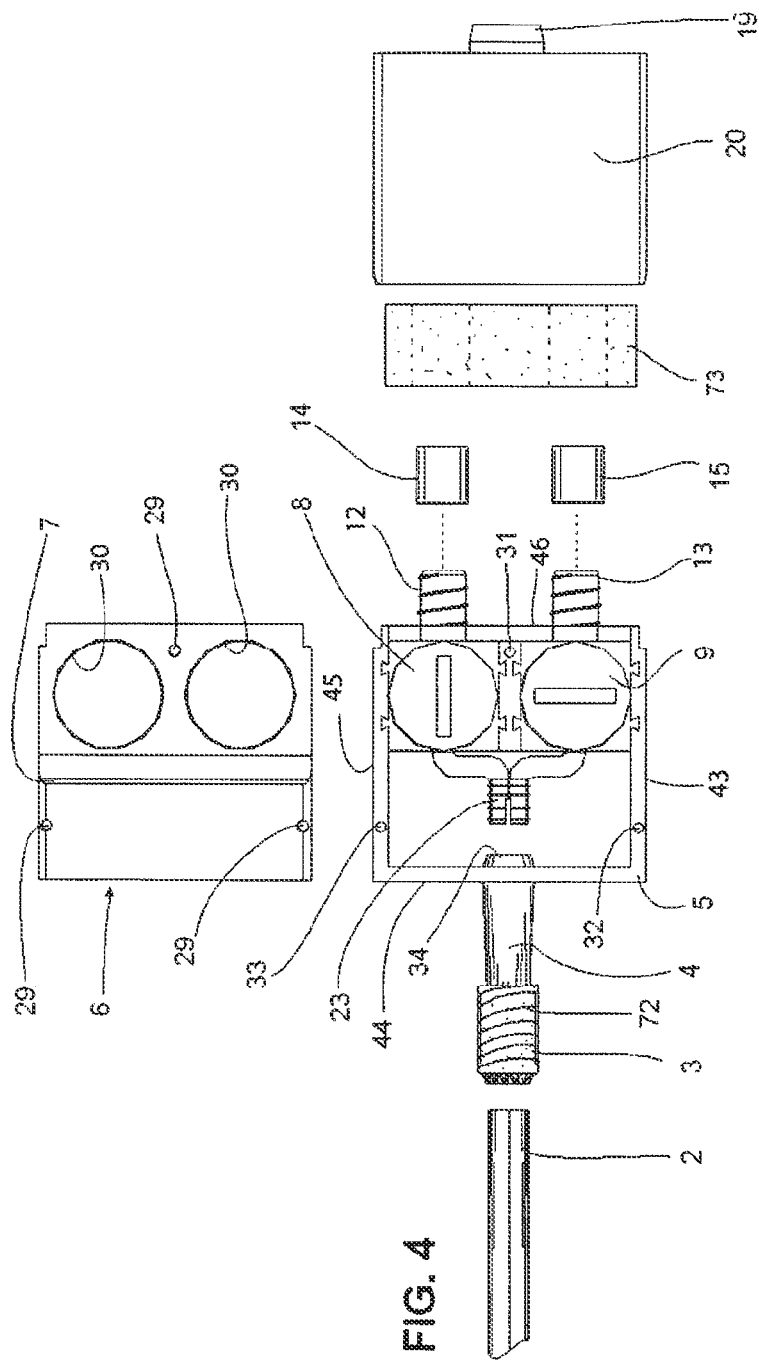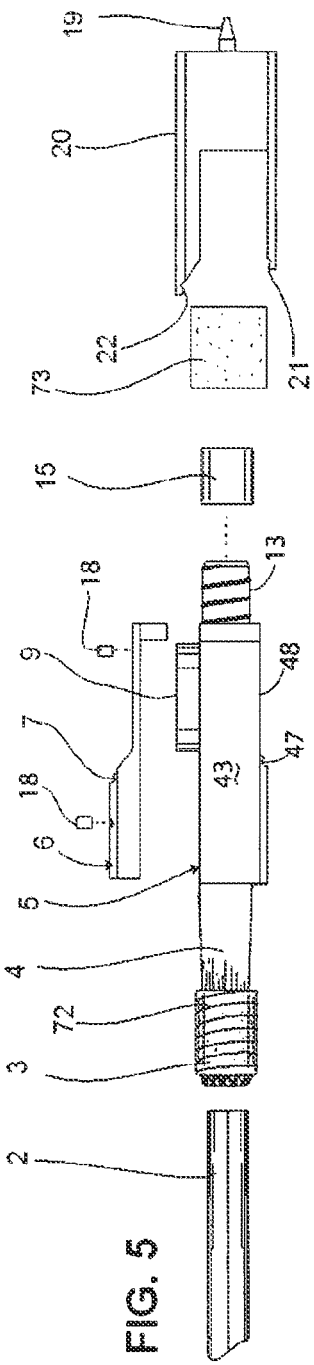
FIG. 4
FIG. 5

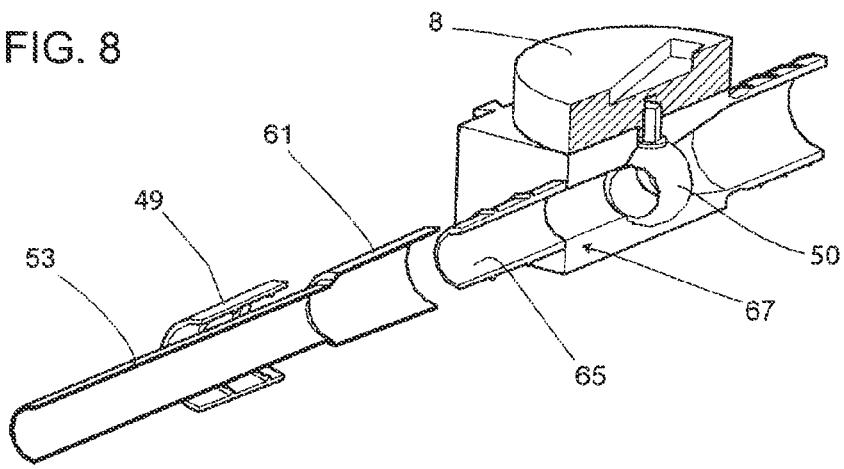
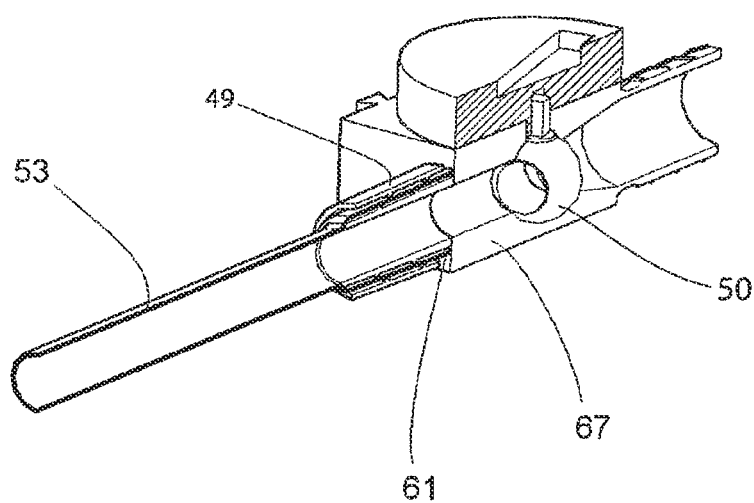
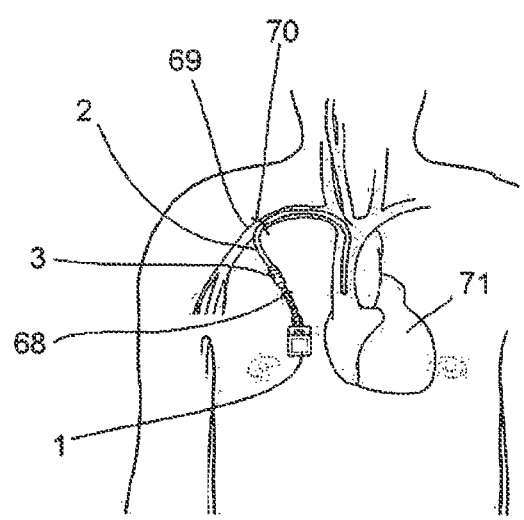

EXTERNAL END DEVICE FOR PERMANENT CATHETERS

TECHNICAL FIELD

The present invention relates to an external end device for permanent catheters, that is useful for example in dialysis and chemotherapy, and a method for implanting it in a body of a patient.

BACKGROUND ART

Some documents of the state of art disclose catheters that are provided with connection devices located outside of the body of a patient with particular respect to the problem of maintaining aseptic conditions.

Patent EP 0 070 087 discloses a connector member, comprising a valve adapted to a ultraviolet antimicrobial irradiation, the connector member being able to connect a permanent catheter to an external equipment. The above patent describes especially materials to be used to make the connector member, materials that have to be permeable to ultraviolet rays and, at the same time, resistant to them. However, said patent considers neither any closure means for the connector member when the latter is not connected to an external equipment, nor any problem relevant to the replacement of a permanent catheter in case of need.

Patent EP 0 227 219 describes a closure plug for an end of a permanent catheter, the closure plug being formed by two detachable parts, the one for keeping aseptic the external side of said end, the other the internal side. For this purpose a material impregnated with an antiseptic liquid is used.

U.S. Pat. No. 5,324,274 discloses a dual lumen vascular access catheter having a main elongated body defining first and second lumens, and a connection structure which includes coupling means attaching the structure to the main body. First and second channels extend from the respective first and second lumens for attaching the catheter to equipment. Further, first and second rotary valves are positioned in the first and second channel. The valves include rotatable operators for providing a ready visual indication of the positions of the valves. U.S. Pat. No. 5,324,274 deals with the connection between equipment and not permanent catheter and then does not face implantation and replacement problems.

The present invention relates to permanent catheters being used for example in dialysis and chemotherapy. Such catheters, made of a deformable, biocompatible material, can have a single lumen or a dual lumen, i.e. two ways. In the to-day permanent catheters near the external end thereof, there is a so called catheter cuff in the form of a thickness. The cuff, that can be made by pure silicone or Dacron filaments, is positioned in the subcutaneous tissue when the same catheter is being implanted. Once the body has developed a reactive fibrous tissue around the catheter, the cuff acts to anchor the catheter to the subcutaneous tissue, preventing or limiting a displacement or an accidental unthreading of the catheter. In the cuffs made of Dacron, the reaction of the subcutaneous tissue to the cuff also constitutes an effective barrier to the bacterial progression along the catheter, and then a limitation to infections. In the most external ends of the catheters, beyond the cuffs, there are end portions, sometimes made of a material different from that one of the catheter, in any case biocompatible and elastic, being provided with standard connectors known as "Luer Lock", which allow catheters to be connected to blood lines of an equipment, for example a dialysis equipment.

These end portions are provided with suitable threaded closure plugs and small clips. The clips once closed squeeze the same end portions and achieve a further safety closure. At last the clips yields the material of the end portion with consequent break, if any, thereof.

The assembly of catheter, cuff, end portion and clip, has several drawbacks, such as, for example, a chronic exposure of the catheter and end portions to the saprophytic bacterial flora existing in the cute of the patient. Up to now the permanent catheters of the above type are fixed sub cute by a cuff; in their extracorporeal section, the permanent catheters are easily attached and infected by a series of pathogen agents as the catheters have to be handled and maneuvered by the nursing.

Initially, the bacterial flora colonizes and then infects the same catheter, first in its exit zone from the cute and then in the internal track thereof, in the subcutaneous tunnel until the catheter enters a vein, obliging its replacement in order to prevent a real septicemia to be developed. As the cuff is integral with the catheter on one side and is incorporated in the subcutaneous reactive tissue on other side, the catheter must be replaced by a surgical operation. In fact, the cuffs being integral with the catheter have to be unbridled from the subcutaneous tissue.

The noise to the patient by the external end portions that are too long and approximately protected by gauzes being wrapped up the external end portions and fixed thereto by plasters is not to be neglected. In a likely way these portions constituted by the external parts of the catheters and by Luer Lock connectors, can get entangled in dresses. The external end portions being free of moving cause esthetical inconveniences due to their cumbersome appearance and can be unintentionally damaged or torn away in sleep or further accidentally opened by the patient without realising and calling for help.

DISCLOSURE OF INVENTION

The present invention aims at overcoming the above mentioned drawbacks and troubles.

An object of the invention is to provide an external end device for permanent catheters that is able to isolate the catheter from the external environment and then from the pathogen agent attack.

Another important object of the invention is to provide an external end device for permanent catheters that allows a permanent catheter to be replaced in a simple way and without a surgical operation.

Yet an object of the invention is to provide an external end device for permanent catheters in which the catheter has no closure clamps or other mechanism yielding it.

Further an object of the invention is to make an external end device for permanent catheters without evident unaesthetic dangerous appendixes hanging from the chest of the patients.

Another object of the invention is to make a little device that can be easily hidden and protected more reliably and with a really better psychological impact for the patient.

For achieving the above objects, the invention in a first aspect thereof provides an external end device for permanent catheters, comprising a container that can be connected at one hand to at least a catheter, and at the other hand to a closure lid containing a disposable absorbent material impregnated by an antiseptic substance, said container housing two taps being provided with knobs operable from outside of the container and having, at one hand, first connectors for the connection to the catheters and, at the other hand, second connectors projecting from the container for the connection to an external equipment, the first connectors being connected to the catheters by at least a coupling exiting the container and externally holding a cuff designed to be positioned in the subcutaneous tissue of the patient's body, the second connectors being provided with caps surrounded by the disposable absorbent material that is received in the closure lid and has spaces for housing the caps so that the absorbent material adheres to the caps for protecting them externally from a bacterial attack by means of the antiseptic substance by which it is impregnated.

In a second aspect, the invention provides an implantation method of an external end device for at least a catheter being inserted through a first skin breach created in the patient's body to reach a central vein, comprising steps of inserting in the free end of the catheter a tunnelling mandrel, that is driven in correspondence of the first skin breach, fed in the thickness of the sub cute and then brought out through a second skin breach, thereby forming a subcutaneous tunnel; positioning the catheter in the subcutaneous tunnel; feeding the catheter, being yet hooked to the tunnelling mandrel, along a coupling being provided with a cuff, the coupling being connected to an external end device for permanent catheters; sub cute positioning the cuff of the coupling and closing by stitches the second skin breach causing the cuff to be fixed in that subcutaneous position for the period necessary for the body to develop around the cuff a fibrous tissue that imprisons and anchors the cuff to the subcutaneous tissue; disconnecting the tunnelling mandrel and adjusting the length of the catheter; and connecting the taps to the catheter and positioning them in the device.

It should be understood that the cuff being bridled in the subcutaneous tissue is a part of the coupling of the external end device and does not belong in any way to the catheter that is freely sliding through the same coupling. Therefore, in order to replace the catheter, it is enough to open the device, to remove the taps, to disconnect the catheter and, after positioning a guide wire inside of its lumen, to unthread the catheter. Once the old catheter is removed, a new catheter is threaded by using the same guide wire temporary left in place, the new catheter being in turn positioned and dimensioned according the measure of the old catheter and connected again to the tap. The above is done without anesthesia, without surgical operation, without any physical and psychological trauma for the patient. Should also one tap be removed, the removal can be performed with the tap yet hooked to the catheter: once the tap is opened, its lumen will be aligned with the catheter's lumen.

BRIEF DESCRIPTION OF DRAWINGS

Further features and advantages will be more evident in the present description of preferred and not exclusive embodiments of an external end device for permanent catheters shown by way of an example and not limiting way with the aid of the enclosed drawing sheets in which:

FIG. 4 shows an exploded top plan view of the device in FIG. 1;

FIG. 5 shows an exploded side view of the device in FIG. 1;

FIG. 8 shows a longitudinally cross-sectioned perspective view of a tap in the device in FIG. 7, being separated from a catheter;

FIG. 9 shows a longitudinally cross-sectioned perspective view of a tap in the device in FIG. 7, being connected to a catheter; and FIG. 10 is a diagrammatic fragmentary view of a human body shown in transparence, in which a device according to the first embodiment of the invention is positioned.

DETAILED DESCRIPTION OF EMBODIMENTS

Figure 1:
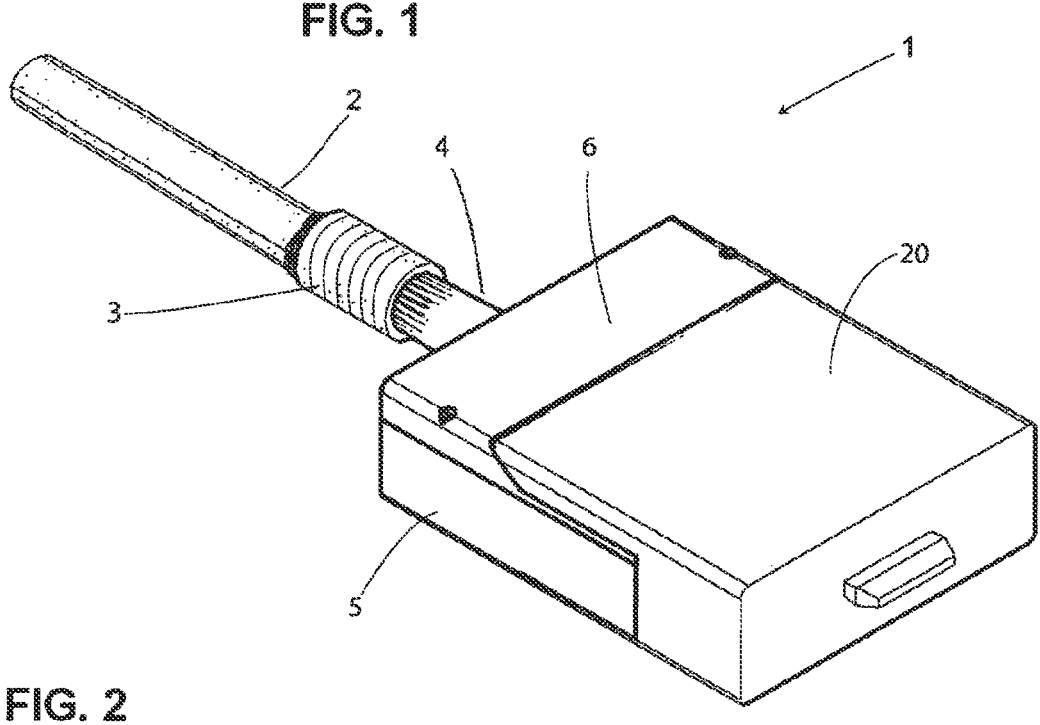
FIG. 1 shows a general perspective view of a first embodiment of the device according to the invention, in a closed position.

In the general perspective view in FIG. 1 an external end device for permanent catheters in a first embodiment for dual lumen catheters, i.e. two way catheters, according to the present invention is indicated as 1. In FIG. 1 a catheter is designated as 2, a subcutaneous cuff 3 is shown surrounding a coupling 4 projecting from a base housing 5 of the device 1, and a covering element of the base housing 5 is indicated as 6. A closure lid of the device 1 is designated as 20.

Figure 2:
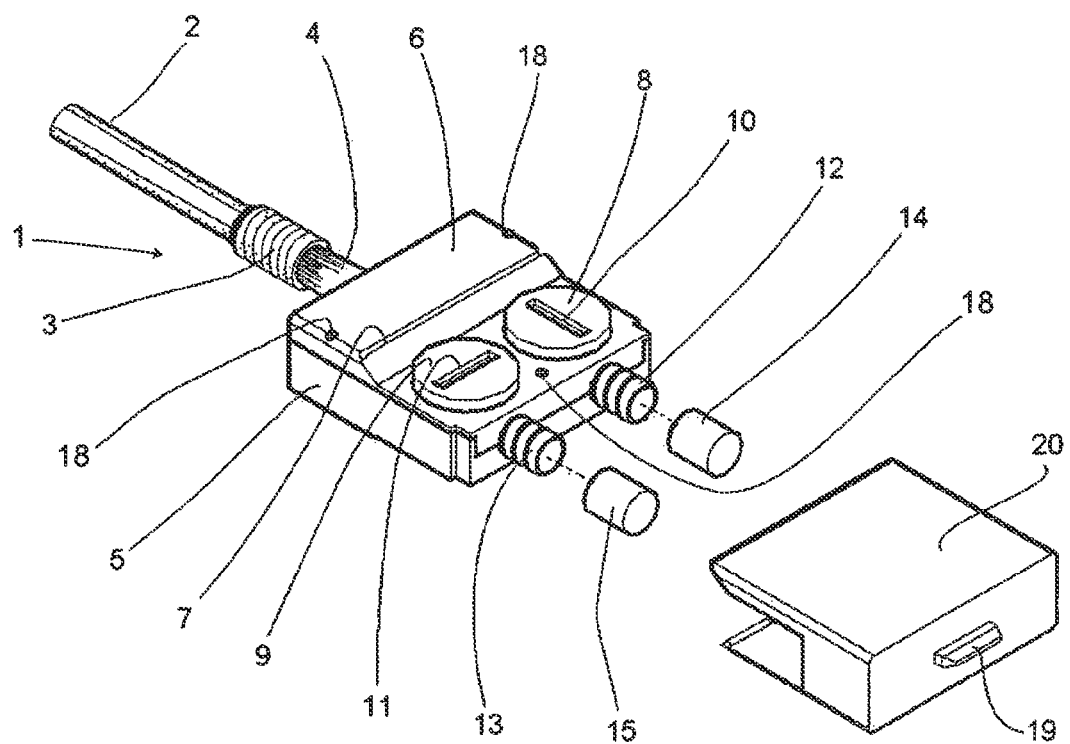
FIG. 2 shows a partially exploded perspective view of the device in FIG. 1.

In the partially exploded perspective view in FIG. 2 the closure lid 20 is separated from the rest of the device. Formed in the covering element 6 is a transversal groove 7 to allow the closure lid 20 of the device to be snap hooked as shown in following figures. Indicated as 8 and 9 respectively, is a knob of relevant tap 26, 27 being housed inside the base housing 5, as shown in the further exploded perspective view in FIG. 3. Notches 10, 11 are provided in the knobs 8, 9 respectively, of the taps 26, 27. The notches 10, 11 serve to turn the knobs 8, 9 as said below. Further, the knobs 8, 9 indicate per se the opened or closed position of the respective tap 26, 27. In their side facing a not shown processing equipment, the taps 26, 27 have Luer Lock connectors 12, 13 provided with caps 14 and 15. Fixing screws generally indicated as 18 fix the covering element 6 to the base housing 5.

The closure lid 20 serves to protect the knobs 8, 9 and the Luer Lock connectors 12, 13, also called below second connectors, as well as the respective caps 14, 15. Formed on a front side of the closure lid 20 is a screwdriver tip shape projection 19, being adapted to be inserted in the notches 10 and 11 for rotating the knobs 8, 9 of the taps 26, 27.

Figure 3:
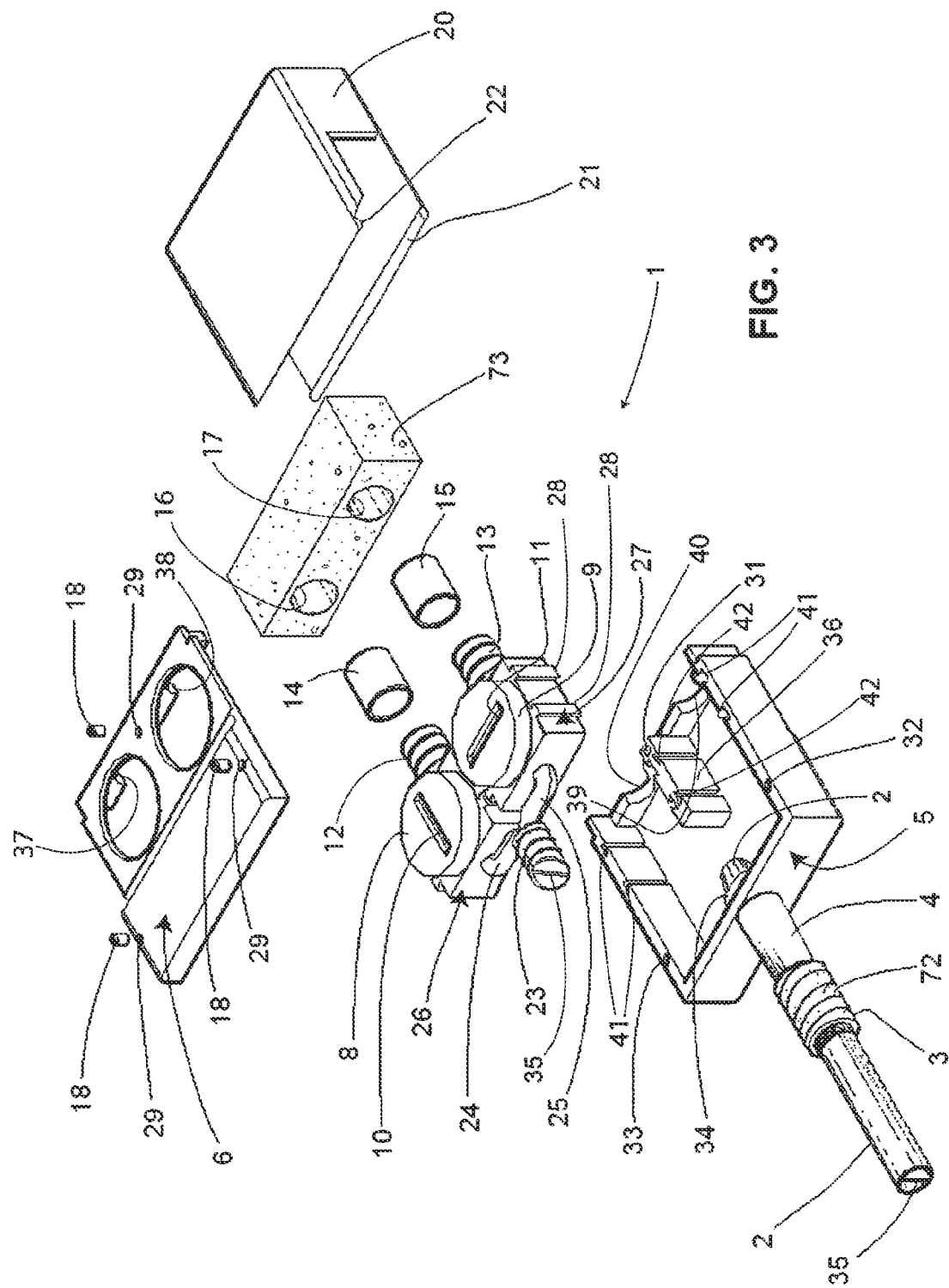
FIG. 3 shows an exploded perspective view of the device in FIG. 1.

In FIG. 3, in addition to the already cited parts, ridges of the lower and upper internal edge of the closure lid 20 are indicated as 21 and 22. The ridges 21, 22 are designed to snap fit in the groove 47, which is provided in the bottom 48 of the base housing 5 (as shown in the exploded side view of the device in FIG. 5) and in the groove 7 above mentioned, respectively, when the closure lid 20 is positioned.

A first connector indicated as 23 connects the catheter 2 to the taps 26, 27 through respective small pipes 24, 25 that can be die-cast with the taps. As said before, the catheter 2 is a dual lumen catheter; also the connector 23 inside the base housing 5 of the device 1 is a dual lumen connector. Two ways are obtained by a septum designated as 35.

Provided on the covering element 6 are holes, generally indicated as 29, for the passage of the screws 18, which are intended to screw in respective holes 31, 32 and 33 made along the perimeter in the base housing 5. The base housing 5 is of a prismatic shape, even if this shape has not to be intended as limiting, and has a bottom 48 and side walls that can be best seen in the top plan view of FIG. 4. A rear wall, i.e. facing the catheter 2, is indicated as 44, side walls as 43 and 45, and indicated as 46 is a front wall of the base housing 5 facing the equipment when the device 1 is being used.

A collar 34 of the coupling 4 extends inside of the base housing 5 through its rear wall 44 and perfects the connection of the coupling 4 integral with the rear wall 44. An internal central septum 36 elevates from the bottom 48 of the base housing 5 with the purpose of anchoring thereto the body of the taps, as shown more in detail below. Referring again to FIG. 3, indicated as 72 is a silver wire emerging from the subcutaneous cuff 3 for a katadyn effect or purification by katadyn process. Housed inside the closure lid 20 is a prismatic-shaped disposable absorbent material 73, impregnated with an antiseptic substance. The disposable absorbent material 73, being spongy for example, engages greatly the caps 14 and 15 by virtue of two correspondent spaces 16, 17 made in the material 73. The diameter of the spaces 16, 17 is lightly lower than that of the caps 14, 15 so that the absorbent material can adhere to and protect them with the action of the antiseptic substance.

Parts already described in preceding figures relating to the first embodiment according to the invention, are shown for clarity sake in the orthogonal views in FIGS. 4 and 5. In particular the housing of the taps 26, 27 is shown. The external body of the taps is of prismatic shape and has dovetail shaped projections 28 on two opposite sides thereof. Correspondingly, dovetail shaped grooves generally indicated as 41 and 42 are made on opposite sides 43, 45 of the base housing 5 and on the central septum 36. The projections 28 and the grooves 41, 42 constitute respectively tenons and mortises for interlocking couplings among the taps 26 and 27 and the base housing 5.

Circular openings 30 (FIG. 4) adapted to allow the knobs 8, 9 of the taps 26, 27 to be operated are provided on the covering element 6. The covering element 6 and the base housing 5 on the front side 46 thereof have half-cylindrical openings 37, 38 and, 39, 40, respectively in order to form a pair of cylindrical openings from which the Luer Lock or second connectors 13 and 12 exit.

Figure 6:
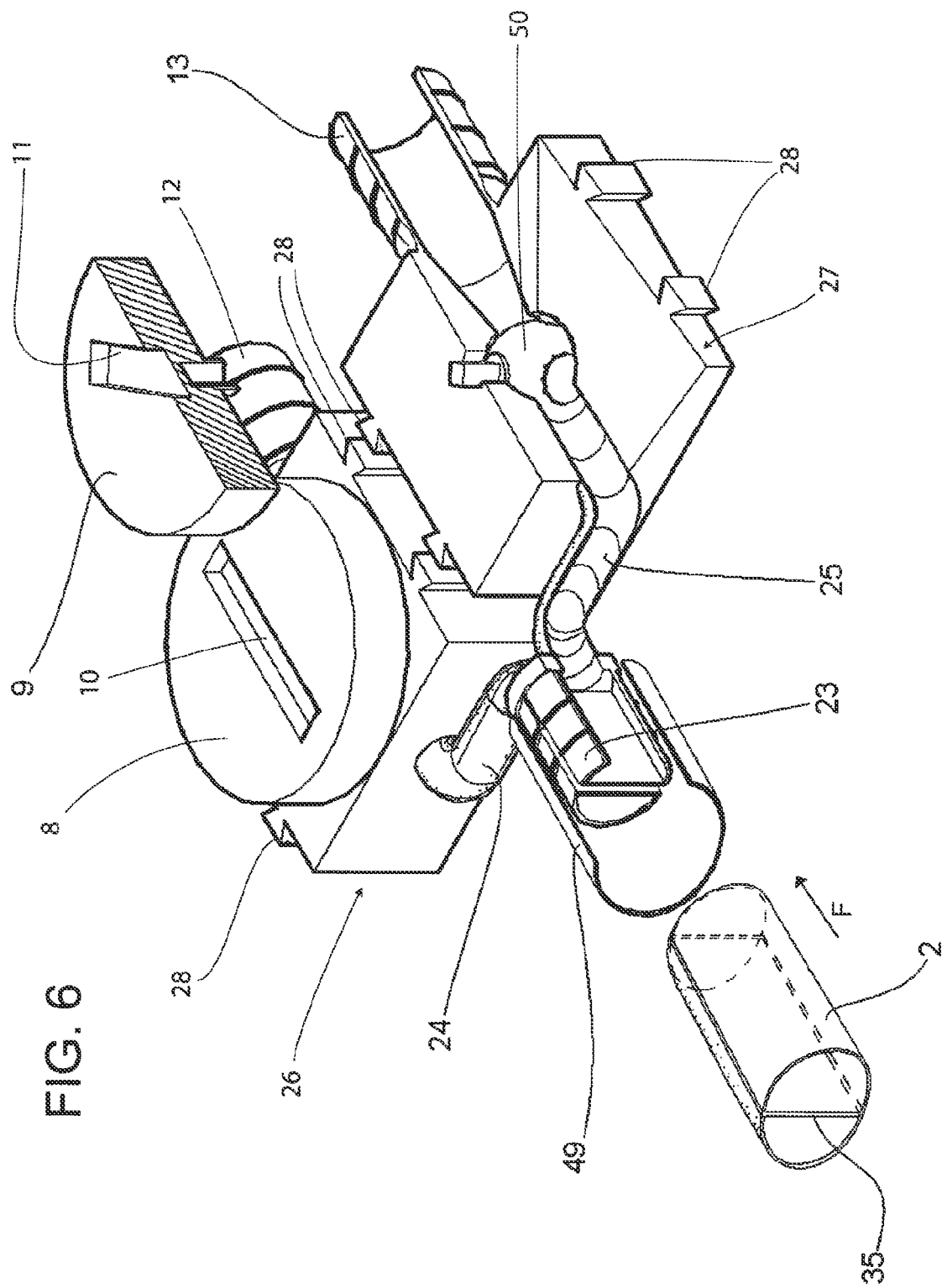
FIG. 6 shows an enlarged partially cross-sectioned exploded perspective view of internal components of the device in FIG. 1.

The taps 26, 27 are shown in detail in FIG. 6, that is an enlarged partially cross-sectioned exploded perspective view of internal components of the device. Particularly illustrated are the dovetail projections 28 and a spherical closure element 50 traditionally operating in the taps and for this reason not described in detail. As shown in FIG. 6, the connection between the catheter 2 and the internal connector 23 according to the arrow F is perfected by a hose clamp 49.

Figure 7:
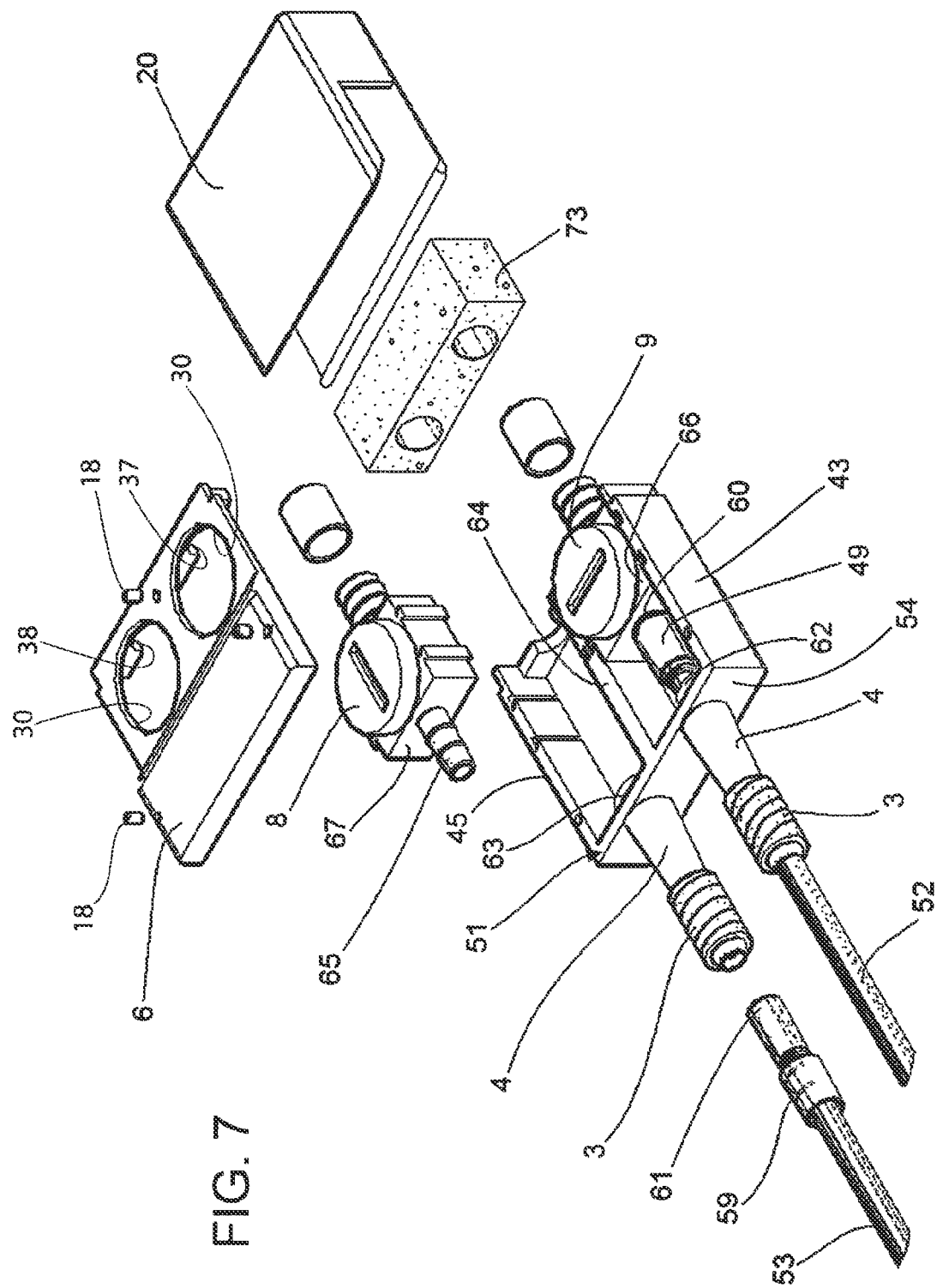
FIG. 7 shows a general exploded perspective view of a second embodiment of the device according to the invention.

Shown in FIG. 7 in an exploded perspective view is a second embodiment of the external end device according to the invention for two single-lumen catheters that is shown also in longitudinally cross-sectioned perspective details in FIGS. 8 and 9. In these figures same reference numerals of the first embodiment of the invention are used for indicating equal or similar parts.

In FIG. 7, in addition to elements already defined, the base housing of the second embodiment of the device is indicated as 51, single-lumen catheters as 52, 53, each of two subcutaneous cuffs like those in the first embodiment as 3, relevant couplings as 4 being integral with the wall 54 of the base housing 51. Ends of the couplings 4 inside the base housing 1 are indicated as 62, 63. The catheters 52, 53 being connected to respective taps 66, 67 project in the base housing from such ends of the coupling 4. The taps 66, 67 are received inside the base housing 51 with tenons and mortises similar to that already described for the first embodiment. The mortises are made on a central septum 64 extending throughout the length of the base housing 5. First connectors, of which only one indicated as 65 is shown in FIG. 7, project from the taps 66, 67 towards the catheters 52, 53. The connection among the catheters and the first connectors is perfected by a hose clamp 49 as in the first embodiment of the device. In particular, the catheter 53 and the first connector 65 are shown in FIGS. 8 and 9, before and after, respectively, the operation of their connection.

In FIG. 10, which is a fragmentary view of a human body shown in transparence, there are indicated, only by way of example, a central vein as 69, a first skin breach of the catheters 2 as 70, whose internal end is in the vein 69, a cardiac muscle as 71, a second skin breach as 68 or point of exit of the catheter 2 after its subcutaneous track.

An implantation of a device according to the present invention is described below with reference to FIG. 10. For clarity sake, by way of an example, a dual lumen catheter 2 is considered for implanting the above described device 1 in the patient's body.

The catheter 2 is introduced by using the well-established Seldinger technique. At the end of this operation, the catheter 2 on one hand exits the first skin breach 70 created for accessing to the central vein 69, and on the other hand it remains well positioned in the lumen of the same vein. At this point, inserted in the free end of the catheter 2 is a tunnelling mandrel (not shown), that, being infixed in the layer of the subcutaneous tissue in the place in which the first skin breach 70 is performed corresponding to the central vein 69, is fed in the same subcutaneous layer for a few centimeters and then emerges again outside on the skin surface in the second skin breach 68. In this track the catheter 2 follows the tunnelling mandrel to which it is connected, so that, at the end of this operation, the catheter is well positioned in its newly formed subcutaneous tunnel. The tunnelling mandrel, which is suitably shaped in such a way that it does not interfere with the device, is passed through the external device (coupling and base housing); the coupling is positioned in the skin breach, a suture is made for blocking the cuff in the subcutaneous layer, and at this point the tunnelling mandrel is disconnected and the length of the catheter is adjusted.

After disconnecting the tunnelling mandrel, the catheter 2 is accurately positioned, by determining the length in centimeters of its portion to be implanted and that one to be removed, both referring to the centimeters printed on the catheter surface and checking the catheter functionality, i.e. assuring that the catheter provides a suitable blood flow, without any interruption or fits and starts. This can be achieved also using a temporary connection that can simulate for example a dialysis equipment. After this the catheter is connected to the device 1. Advantageously the device is provided in the medical kit with the components being separated, thereby the device does not need to be opened as it is already opened. After connecting the catheter to the tap, the components are assembled and the device is finally closed.

Turning to FIG. 3, the device 1 is opened after detaching the closure lid 20, the covering element 6 is removed by screwing the screws 18 that joint the covering element 6 to the base housing 5, and the taps 26, 27 are removed from the same base housing 5 by sliding them along the dovetail grooves 41, 42. The catheter 2 is passed inside the coupling 4 that is provided with the subcutaneous cuff 3, and is slid along the coupling 4, until the catheter 2 emerges again beyond the internal collar 34 of the coupling 4. A hose clamp 49 (FIG. 6) is then slid along the catheter 2. The cuff 3 is positioned sub cute and the second skin breach 68 is closed by means of suitable stitches causing the cuff 3 to be fixed in that subcutaneous position for the period necessary for the body to develop around the subcutaneous cuff 3 a fibrous tissue that imprisons and anchors the cuff 3 to the subcutaneous tissue. In such a way all the device 1 as illustrated in FIG. 10 is anchored. Now the length of the catheter 2 is reduced to the desired length also considering the above functional evaluations. Then, the catheter 2 is connected to the taps 26, 27 after checking that the latter are closed by manually operating the knobs 8, 9 or the notches 10, 11, by means of the projection 19 provided on the closure lid 20. For connecting the catheter 2 to the taps 26, 27, the connector 23 is inserted inside the end of the catheter 2 exiting the collar 34, causing the septum 35 separating the two catheter ways to be inserted in the adapted notch in the connector 23. By clasping the hose clamp 49 over the portion of the catheter 2 that is inserted in and connected to the connector 23 of the taps 26, 27, a reliability against an accidental mutual disconnection is increased. After positioning the taps 26, 27 in their seats inside the base housing 5, assuring that the Luer Lock connectors 12, 13 are well positioned and project from the opening of the base housing 5 through the openings 37, 38, 39, 40 (FIG. 3), the closure 6 is connected again to the base housing 5 being fixed by screwing the screws 18 in their holes 29. The closure lid 20 is snap hooked after inserting therein the absorbent material 73 containing the antiseptic solution so that a safer barrier to the bacterial attack is assured and an infection occurrence is limited. The entire device 1 is covered with a medical band aid, in order to prevent it to swing, as well as to further protect it from external pollution, if any, until its next use. The post-implant utilisation of the device on the patient consists of its connection to the dialysis equipment by connecting its blood lines to the standard Luer Lock connectors of the device. First the medical band aid protecting the device has to be removed. After removing the closure lid 20, the caps 14, 15 of the Luer Lock connectors 12, 13 are unscrewed. A syringe is connected to the connector 12 and, after opening the knob 8, some blood of the patient is sucked in order to assure that the catheter works and then to remove an antithrombotic solution being therein left at the end of the previous use. After this, the knob 8 is closed, the syringe is detached and the blood line of the dialysis circuit is directly connected to the connector 12. Such an operation is repeated for the connector 13 and the knob 9. At the end of the treatment the above described maneuvers are repeated in reverse order and terminate before positioning the caps 14, 15 with the injection therein of a suitable amount of a physiologic solution for washing connectors and catheters, and then with the injection of a suitable amount of antithrombotic solution in order to prevent clotting inside the catheter between two consecutive treatments (such a last solution being called Filling or also Priming solution must fill the "tap-catheter" system, but has not to be admitted in the blood circulation). Before closing the device by the closure lid 20, a new absorbent material 73 with antiseptic solution is positioned inside of it.

It should be understood that also the replacement of the catheter 2, if any, is simple by means of the device according to the invention. After opening the device 1 by detaching the closure lid 20, removing the covering element 6 and the taps 26, 27 from the base housing 5, the catheter to be replaced is passed by means of guide wires through the coupling 4 that remains fixed to the patient's body through the subcutaneous cuff 3. The new catheter 2 will be inserted in the same central vein by means of the same guide wires and will be slid through the same coupling 4. No bloody operation that can be hazardous for the patient and difficult for the medical operators, is requested for replacing the catheter.

The invention claimed is:

1. An external end device for permanent catheters, comprising:
    a container connectable to one or more catheters and to a closure lid containing a disposable absorbent material impregnated by an antiseptic substance,
    wherein said container houses two taps being provided with knobs operable from outside of the container and having first connectors for connection to the catheters and second connectors projecting from the container for connection to an external equipment,
    the first connectors connectable to the catheters by at least a coupling exiting the container and externally holding a subcutaneous cuff configured to be positioned in a subcutaneous tissue of a body of a patient, and
    the second connectors being provided with caps surrounded by the disposable absorbent material that is received in the closure lid and has spaces for housing the caps such that the absorbent material adheres to the caps for protecting them externally from bacterial attack by means of the antiseptic substance.

2. The device according to claim 1, wherein said first connectors are joined by a connection to at least one coupling inside the container, the connection being assured by a hose clamp surrounding mutual engagement ends of the first connectors and of at least one coupling.

3. The device according to claim 1, wherein said subcutaneous cuff presents silver wires emerging from inside the subcutaneous cuff to a surface of the subcutaneous cuff for a katadyn effect.

4. The device according to claim 1, wherein said container comprises a base housing and a covering element provided with openings to reach the knobs operating the taps.

5. The device according to claim 4, wherein said covering element is removable.

6. The device according to claim 1, wherein each of said knobs has an elongated notch indicating the opening and closure condition of the respective tap, and said closure lid has a screwdriver head shape projection engageable with the elongated notch of the knobs.

7. The device according to claim 4, wherein said base housing is of a prismatic shape having side walls, a rear wall provided with at least a passage hole for a coupling, and a front wall, and an at least partial central septum.

8. The device according to claim 7, wherein the side walls and the central septum have opposite grooves for fixed joint with correspondent projections being formed in the body of the taps.

9. The device according to claim 7, wherein the covering element and the front wall of the base housing are provided with semicircular openings for forming circular passage openings of the second connectors for the connection with the external equipment.

10. The device according to claim 7, wherein the covering element and the front wall of the base housing are provided with transversal grooves for snap engagement with correspondent projections being formed in the closure lid.

* * * * *